US011517327B2

(12) United States Patent
McGinley et al.

(10) Patent No.: US 11,517,327 B2
(45) Date of Patent: Dec. 6, 2022

(54) MULTI-DIRECTIONAL DRILLING FOR PERFORATION OF BONE CORTEX

(71) Applicant: McGinley Engineered Solutions, LLC, Casper, WY (US)

(72) Inventors: Joseph McGinley, Casper, WY (US); Adam M. Johnson, Casper, WY (US); Brian Nolte, Casper, WY (US)

(73) Assignee: McGinley Engineered Solutions, LLC, Casper, WY (US)

( * ) Notice: Subject to any disclaimer, the term of this patent is extended or adjusted under 35 U.S.C. 154(b) by 72 days.

(21) Appl. No.: 17/222,145

(22) Filed: Apr. 5, 2021

(65) Prior Publication Data

US 2021/0322029 A1    Oct. 21, 2021

Related U.S. Application Data

(60) Provisional application No. 63/010,190, filed on Apr. 15, 2020.

(51) Int. Cl.
*A61B 17/16* (2006.01)
*A61B 90/00* (2016.01)
*A61B 17/56* (2006.01)

(52) U.S. Cl.
CPC .... *A61B 17/1626* (2013.01); *A61B 2017/564* (2013.01); *A61B 2090/061* (2016.02); *A61B 2090/064* (2016.02)

(58) Field of Classification Search
CPC .......... A61B 17/1626; A61B 2090/061; A61B 2090/064; A61B 2017/564; A61B 17/1615
See application file for complete search history.

(56) References Cited

U.S. PATENT DOCUMENTS

| 6,665,948 B1 * | 12/2003 | Kozin ................. A61B 90/06 175/45 |
| 9,102,026 B2 * | 8/2015 | Miller ............... B23Q 17/0966 |
| 2015/0066038 A1 * | 3/2015 | McGinley .......... A61B 17/1615 606/80 |
| 2015/0080966 A1 * | 3/2015 | Anderson ............. A61B 17/17 606/280 |

\* cited by examiner

*Primary Examiner* — Kevin T Truong
*Assistant Examiner* — Diana Jones
(74) *Attorney, Agent, or Firm* — Holzer Patel Drennan (57) ABSTRACT

Multi-directional drilling of a bone to create a perforation of bone cortex. The disclosure presents methods of using a drill having a measurement system to advance a drill bit through a bone with detection of penetration or eruption of the leading edge of the drill bit through the exterior of the cortex layer of the bone. In this regard, operation of the drill may be controlled to limit soft tissue damage adjacent to the distal side of the bone. The drill bit may be at least partially retracted through a first bore, repositioned, and one or more additional bores may be created, all while monitoring for penetration of the leading edge of the drill bit relative to the cortical layer. In turn, a perforated distal side of the cortical layer of the bone may be created that creates a desired weakness in the bone, which may be useful in various operations including when performing a corticotomy or the like.

6 Claims, 9 Drawing Sheets

FIG. 9

MULTI-DIRECTIONAL DRILLING FOR PERFORATION OF BONE CORTEX

RELATED APPLICATIONS

This application claims the benefit of provisional application number U.S. 63/010,190, filed on Apr. 15, 2020, entitled "MULTI-DIRECTIONAL DRILLING FOR PERFORATION OF BONE CORTEX", the entirety of which is incorporated herein by reference.

BACKGROUND

In some orthopedic procedures, bones may be entirely or partially cut or sawed to separate all or a portion of a bone. Such operations are typically performed using traditional saw instruments, which can come in a variety of configurations. For instance, sagittal saws, circular saws, reciprocating saws, cut-off wheels on a straight spindle grinder tool, or other instruments may be used in such operations. Alternatively, traditional handheld straight saw blades might be used to cut through a bone. For instance, some orthopedic procedures include a corticotomy to selectively remove the cortex of a bone or separation of a bone. One such example of a procedure including a corticotomy is distraction osteogenesis in which the cortex of a bone may be partially or totally severed leaving at least a portion of the medullary vessels and periosteum intact to allow the bone to be separated for bone regeneration.

In any of these traditional approaches, a significant risk for soft tissue damage exists as each of these approaches rely on a surgeon's skill in manipulating the saw to avoid inadvertent contact with soft tissue surrounding the bone. However, regardless of the skill of the surgeon operating, it may be difficult or impossible to reliably control a saw in all contexts when sawing through a bone. A particular concern relates to the completion of a cut when the saw may experience "plunge" or a rapid acceleration beyond the bone at the completion of the cut. Moreover, to avoid inadvertent soft tissue damage, the bone is often isolated from the soft tissue by manipulating surrounding soft tissue (e.g., retracting or otherwise separating soft tissue from the bone). Manipulation or contact of soft tissue may lead to increased trauma associated with an operation, which may lead to extended healing times and reduces the efficacy of an operation. Accordingly, the need exists for approaches that may efficiently and reliably remove bone cortex while reducing the risk of inadvertent soft tissue damage.

SUMMARY

The present disclosure generally relates to a method for multi-directional drilling of a bone. The method includes drilling a first bore through the bone with a drill bit while monitoring the displacement and force of the advancement of the drill bit relative to a reference point and detecting, based on the displacement and the force, a leading edge of the drill bit in the first bore passing through an exterior portion of a cortex of the bone. The method also includes at least partially retracting the drill bit through the first bore and repositioning the drill bit at a proximal portion of the first bore at an angle with respect to the first bore. In turn, the method includes drilling a second bore through the bone with the drill bit while monitoring the displacement and force of the advancement of the drill bit relative to the reference point, the second bore extending at an angle relative to the first bore and detecting, based on the displacement and the force, a leading edge of the drill bit in the second bore passing through an exterior portion of a cortex of the bone. In turn, a bone may be vented by creating a plurality of bores in the bone to create a perforated portion of the cortex layer 102. The perforated portion of the bone may in turn be strategically weakened to allow for more controlled fracture of the bone or the like.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

DETAILED DESCRIPTIONS

As described above, when performing orthopedic operations, it is advantageous to avoid damage to soft tissue and/or other anatomical structures surrounding a bone. In this regard, many orthopedic operations performed on bones result in damage to soft tissue in the area of the operation. Preferably, techniques and equipment used in such orthopedic procedures reduce or eliminate such soft tissue damage to improve surgical outcomes, minimize the recovery time for such procedures, and generally improve patient care.

In particular, when performing operations such as a corticotomy in which a bone is partially or totally severed, the potential for damage to surrounding structures is high. This is especially true when utilizing traditional sawing instruments that often rely on precise control by a surgeon to minimize ancillary damage to soft tissue at the surgical site. Moreover, use of surgical saws or the like may contribute to heating of the bone at the site of the cut. Such heat generated by the saw may damage the bone tissue and retard healing. Moreover, chisels or osteotomes may be used, but precision may be difficult to achieve. Accordingly, even with the utmost care by surgeons, often time use of traditional approaches suffer from imprecision or result in damage to anatomical structures adjacent to the surgical site.

In this regard, the present disclosure generally relates to use of a drill instrument to help reduce or avoid damage to surrounding structures in a surgical operation. Specifically, a drill instrument having a measurement system that can detect a leading edge of an instrument passing through a cortex layer of the bone may be utilized. In this regard, a plurality of bores may be created using such an intelligent drill such that a bone is at least partially severed while avoiding or minimizing damage to adjacent tissue. For instance, the plurality of bores may be created by drilling from a proximal side of the bone to a distal side. The plurality of bores may be created near a reference point at the proximal side of the bone. The axes of the respective bores may be disposed at an angle to one another such that the bores diverge from the reference point as the bores extend from the proximal side of the bone to the distal side of the bone. Thus, the bores may create a set of bores that create perforations of the bone at the distal side. In turn, the bone may be more easily and precisely separated (e.g., using chisels or osteotomes) with the perforations created by the bores creating an intentional weakness in the bone along which the bone may separate. The multi-directional set of bores may preserve the medullary layer at least intact in areas while allowing selective removal of the cortex layer of the bone. Because the bores are created using the intelligent drilling instrument, the amount of contact between the instrument and the tissue adjacent to the distal side of the bone may be reduced or eliminated. In turn, a relatively small area of the bone at the proximal side may be exposed to perform the drilling operations. Thus, the operation on the bone may be accomplished with very little of the bone exposed at the proximal side of the bone and with very little contact with tissue adjacent to the distal side of the bone. Moreover, heating of the bone tissue and/or surrounding tissue may be reduced as compared to use of a saw instrument, thus preserving the viability of the bone tissue adjacent to the bores.

Accordingly, the following discussion includes a description of a technique used to create the bores through a bone. In addition, a discussion of an example drilling instrument with an integrated measurement system is presented that may be used to create the bores with detection of the interface between the cortex layer and an exterior of the bone. While examples of such an intelligent drill having interface detection are described and incorporated by reference herein below, it may be appreciated that any instrument capable of detecting such an interface may be used in conjunction with creation of a bore structure in a bone as described herein.

Figure 1:
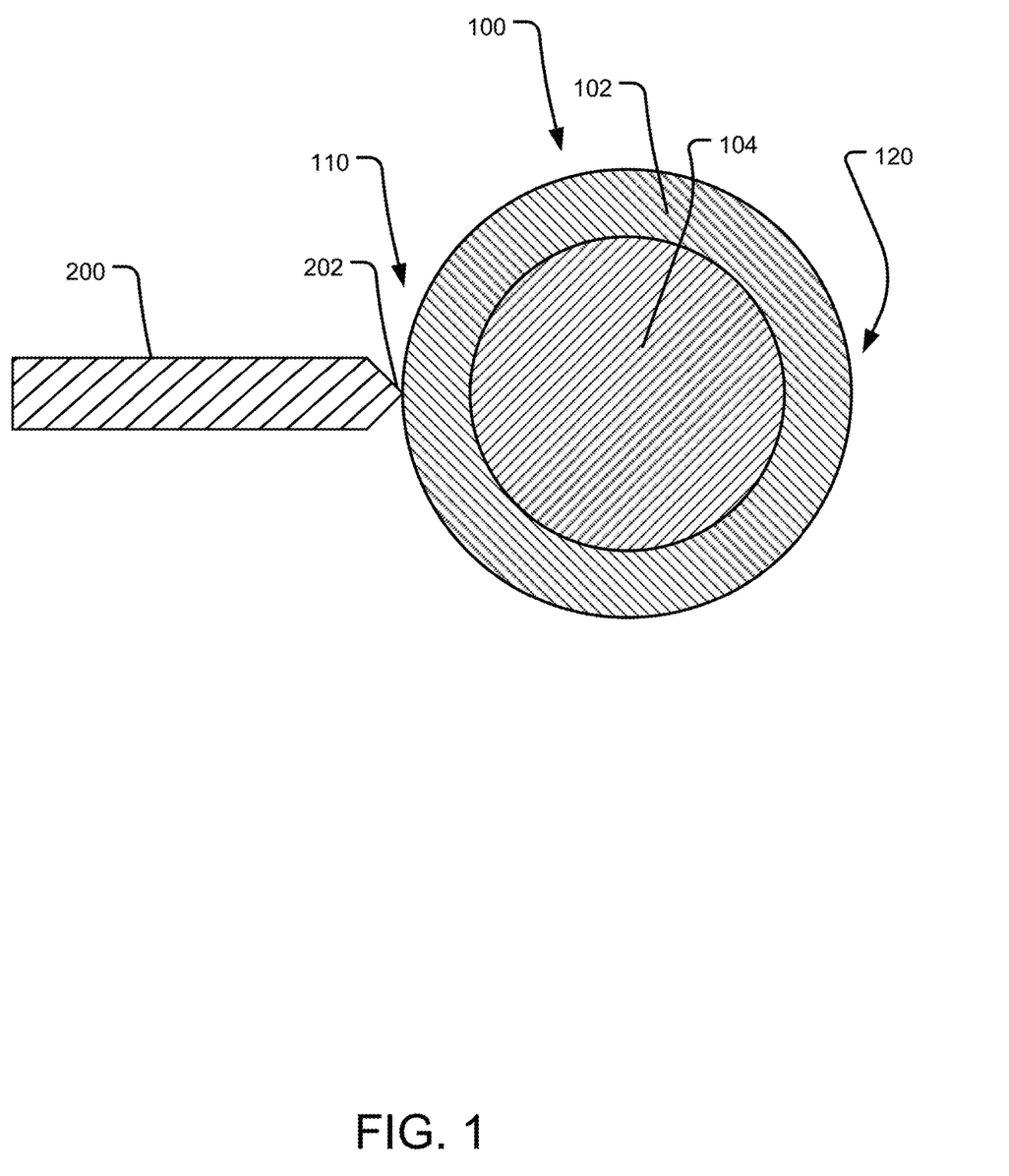
FIG. 1 is a partial cross sectional view of an example of a drill bit positioned relative to a bone to be drilled.

FIG. 1 depicts a bone 100 depicted in cross section. The bone 100 includes a hard outer cortex layer 102 and an medullary layer 104. As shown in FIG. 1, the bone 100 may be a long bone that is generally cylindrical such that the cross section of the bone 100 appears as concentric circles with the cortex layer 102 surrounding the medullary layer 104. However, it should be appreciated that the discussion presented herein is generally applicable to any bone type without limitation.

FIG. 1 also depicts a drill bit 200 having a leading edge 202. While not shown, the drill bit 200 may be engaged with a drill or other device that may impart rotational motion to the drill bit 200. Specifically, the drill bit 200 may be engaged with a drill having a measurement system capable of measuring the displacement of the leading edge 202 of the drill bit 200 with respect to a reference point and a force sensor capable of measuring an axial force acting on the drill bit 200 as the drill bit 200 is advanced relative to the bone 100.

Figure 2:
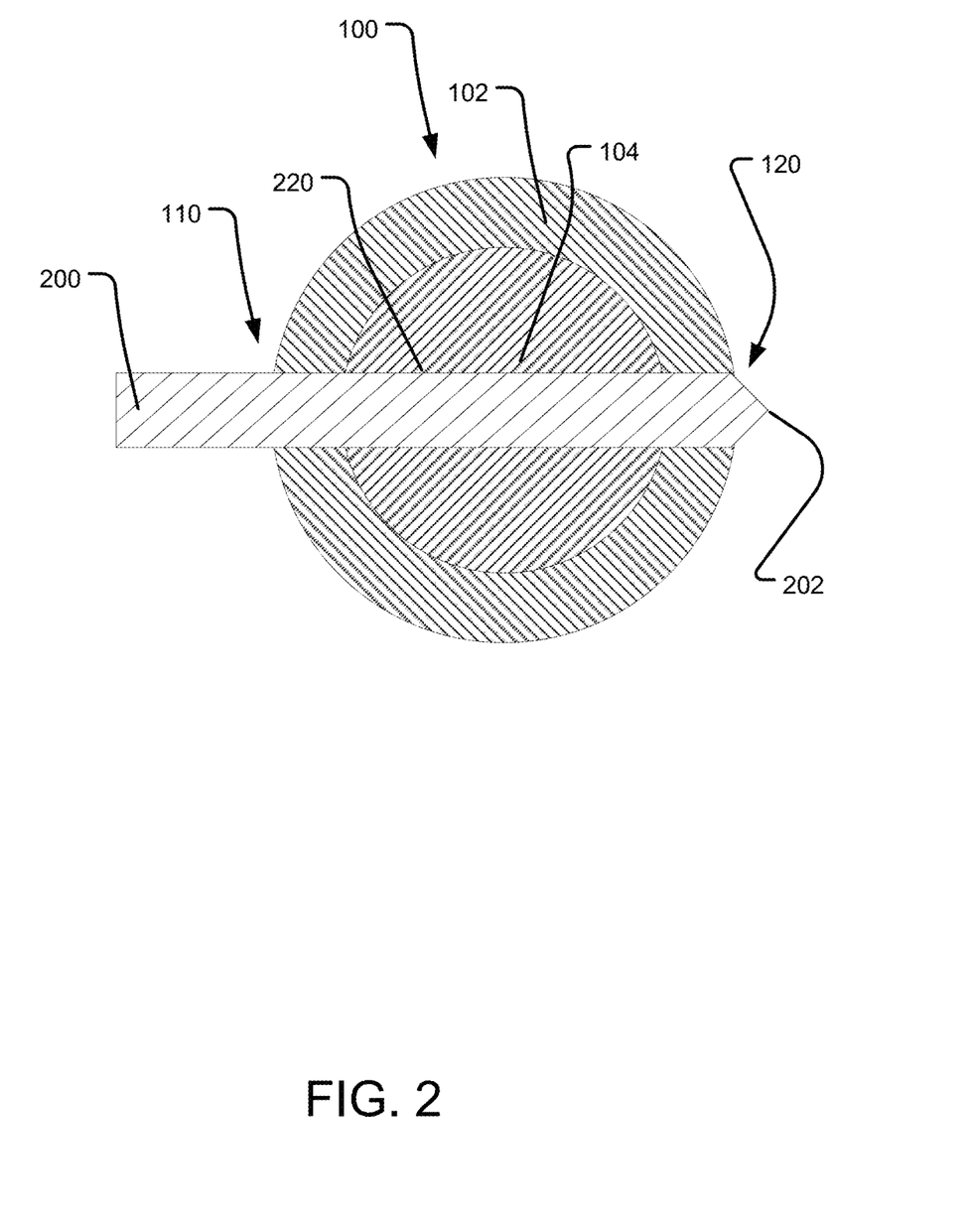
FIG. 2 is a partial cross sectional view of an example of a drill bit having drilled a first bore relative to a bone to be drilled.

In any regard, the leading edge 202 of the drill bit 200 may be disposed at a proximal side 110 of the bone 100. This may be used as a reference point relative to which the advancement of the drill bit 200 may be measured. In this regard, the drill bit 200 may be rotated by the drill to advance the drill bit 200 relative to the bone 100 to create a first bore 220 as shown in FIG. 2. That is, the first bore 220 may be created by the drill bit 200 as it is advanced from the proximal side 110 of the bone 100 to the distal side 120 of the bone 100. The measurement system of the drill used to advance the drill bit 200 may detect the leading edge 202 as it begins to erupt from the cortex layer 102. Specifically, once the drill bit 200 has erupted through the cortex layer 102 as shown in FIG. 2, the measurement system of the drill may cease rotation of the drill bit 200. This may reduce or preclude contact with soft tissue adjacent to the distal side 120 of the bone 100.

Figure 3:
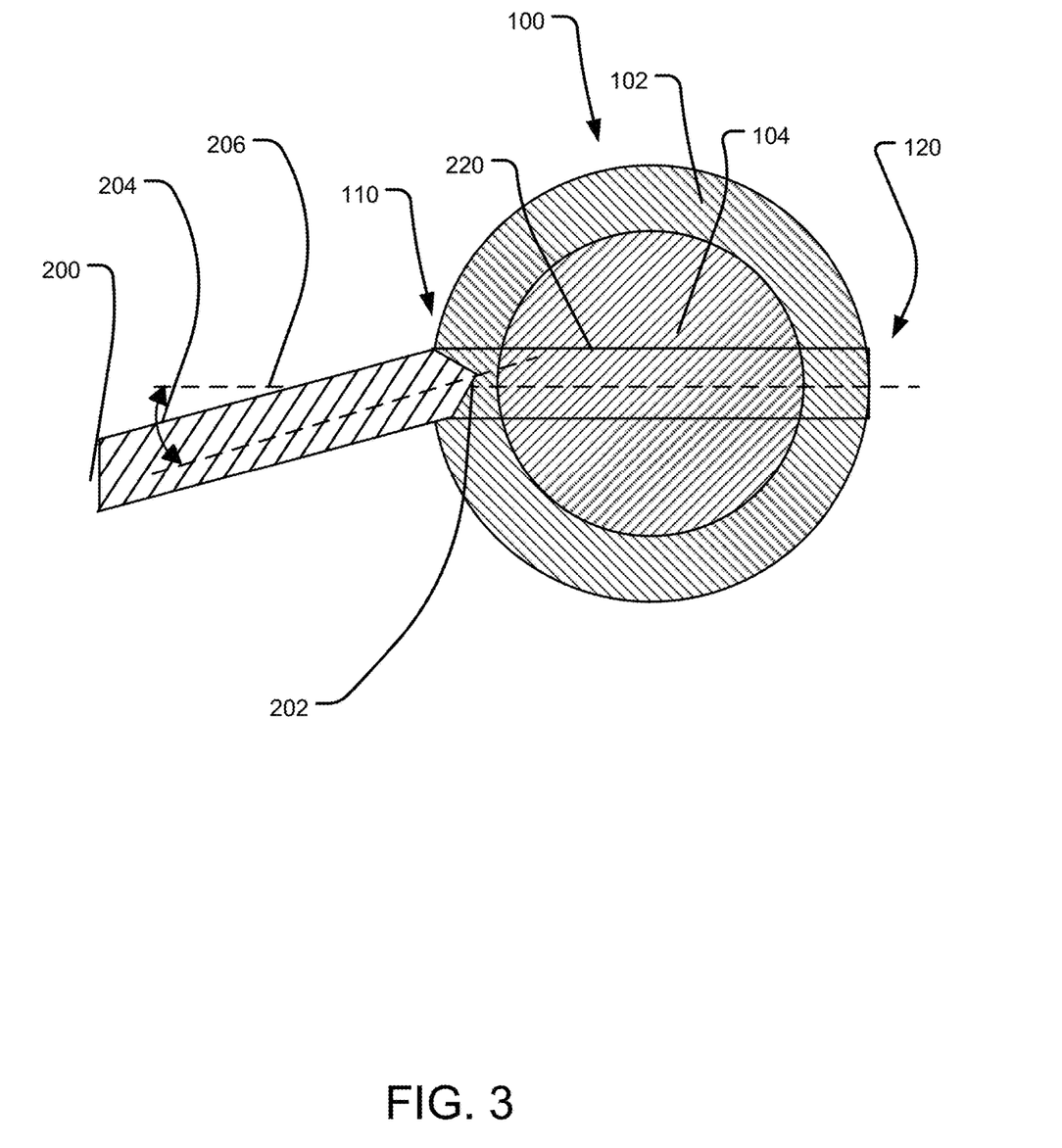
FIG. 3 is a partial cross sectional view of an example of a drill bit that has been retraced relative to a bone to be drilled and repositioned.
Figure 4:
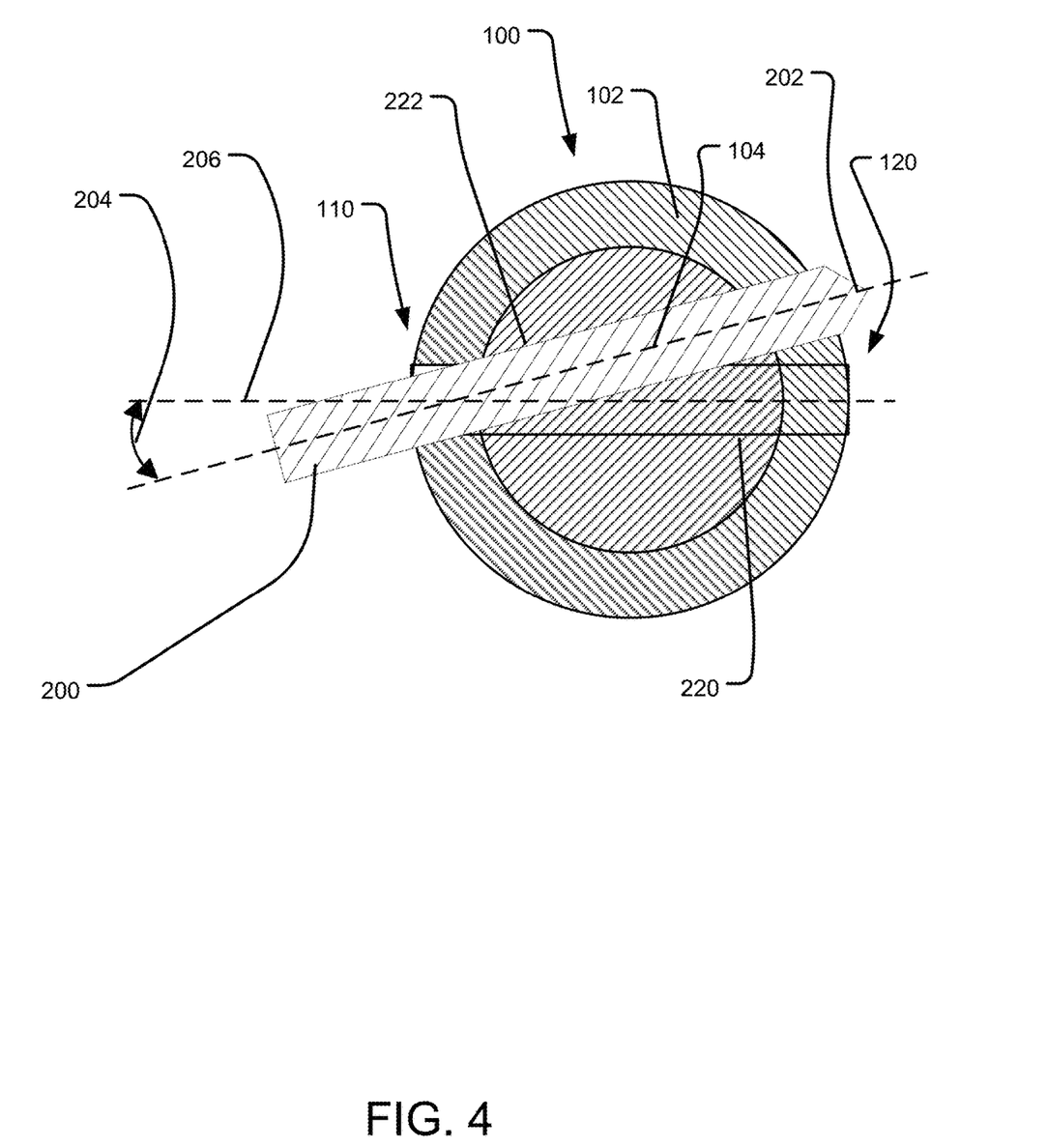
FIG. 4 is a partial cross sectional view of an example of a drill bit having drilled a second bore relative to a previously drilled first bore.

The drill bit 200 may be at least partially retracted from the first bore 220 as shown in FIG. 3. For example, the leading edge 202 of the drill bit 200 may remain in the first bore 220, while the drill bit 200 is repositioned. In turn, the drill bit 200 may be repositioned to be at an angle 204 relative to an axis 206 of the first bore 220. The drill bit 200 may again be advanced axially after repositioning to define a second bore 222 as shown in FIG. 4. In this regard, the first bore 220 and the second bore 222 may share a common entry point at the proximal side 110 of the bone 100. The axis 208 of the second bore 222 is at the angle 204 at which the drill bit 200 was repositioned upon the initial retraction after creating the first bore 220. When the drill bit 200 is advanced in the second bore 222, the measurement system of the drill to which the drill bit 200 is engaged may determine when the leading edge 202 of the drill bit 200 erupts from the cortex layer 102. In this regard, like when creating the first bore 220, the second bore 222 may be created such that the drill bit 200 minimally erupts from the cortex layer 102. In this regard, any soft tissue near the distal side 120 of the bone 100 may experience minimal or no contact with the leading edge 202, and thus soft tissue damage may be minimized.

Figure 5:
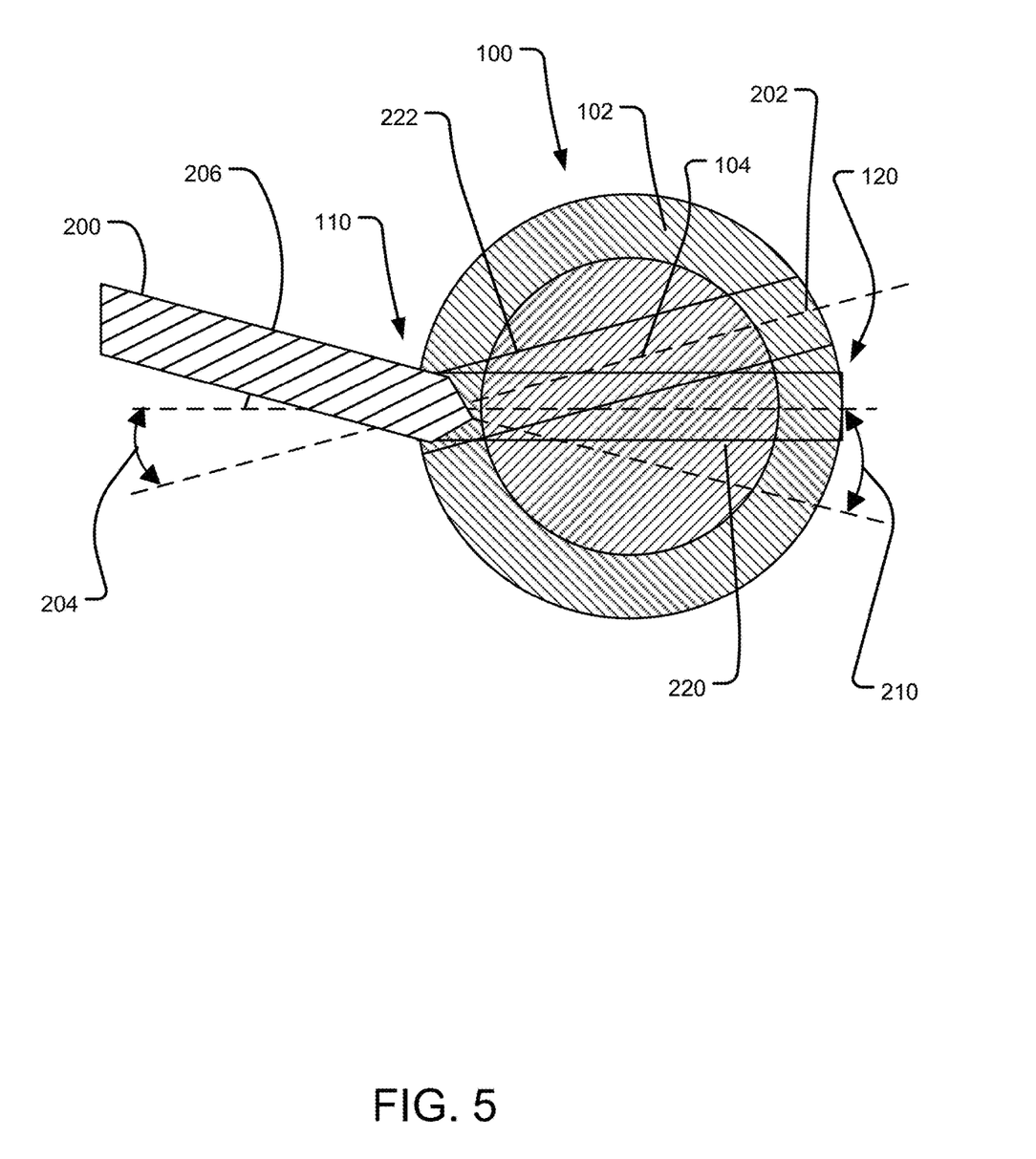
FIG. 5 is a partial cross sectional view of an example of a drill bit that has been retraced relative to a bone to be drilled and repositioned.
Figure 6:
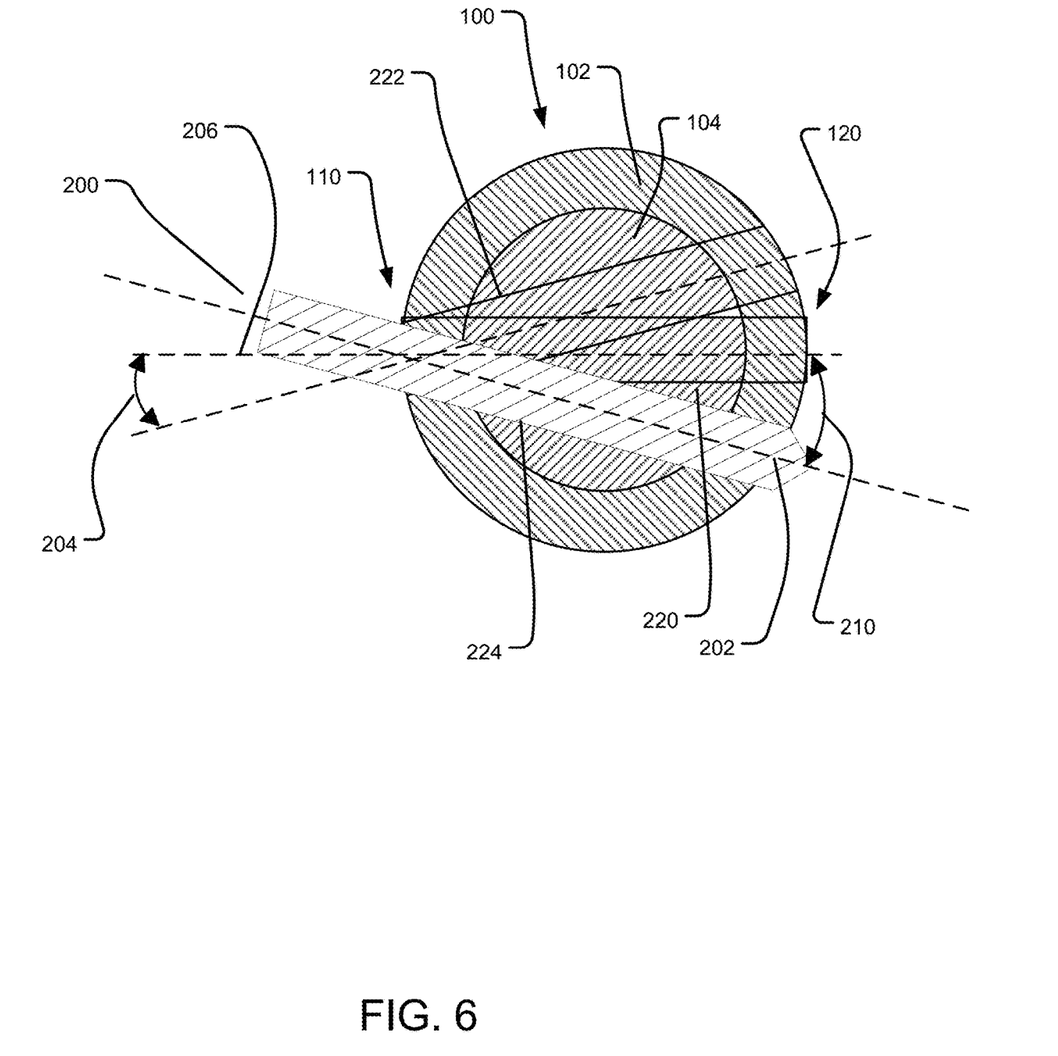
FIG. 6 is a partial cross sectional view of an example of a drill bit having drilled a third bore relative to a previously drilled first bore.

After creating the second bore 222, the drill bit 200 may again be at least partially retracted as shown in FIG. 5. As shown in FIG. 5, the drill bit 200 may again be repositioned relative to the first bore 220 and the second bore 222 to be at an angle 210 relative to the axis 206 of the first bore 220. Again, the leading edge 202 of the drill bit 202 may remain in the original entry point at the proximal side 110 of the bone 100. The angle 210 may be the same as the angle 204 at which the second bore 222 is drilled or a different angle. In any regard, the drill bit 200 may again be advanced as shown in FIG. 6 to define a third bore 224. The third bore 224 may also share an entry point with the first bore 220 and the second bore 222. As each subsequent bore is defined, the drill bit 200 may be monitored using the measurement system of the drill to detect eruption of the leading edge 202 of the drill bit 200. Upon detection of the leading edge 202 passing through the exterior of the cortex layer 102, the user may be alerted and/or the rotation of the drill bit 200 ceased to reduce or preclude soft tissue damage to the tissue adjacent to the distal side 120 of the bone.

Figure 7:
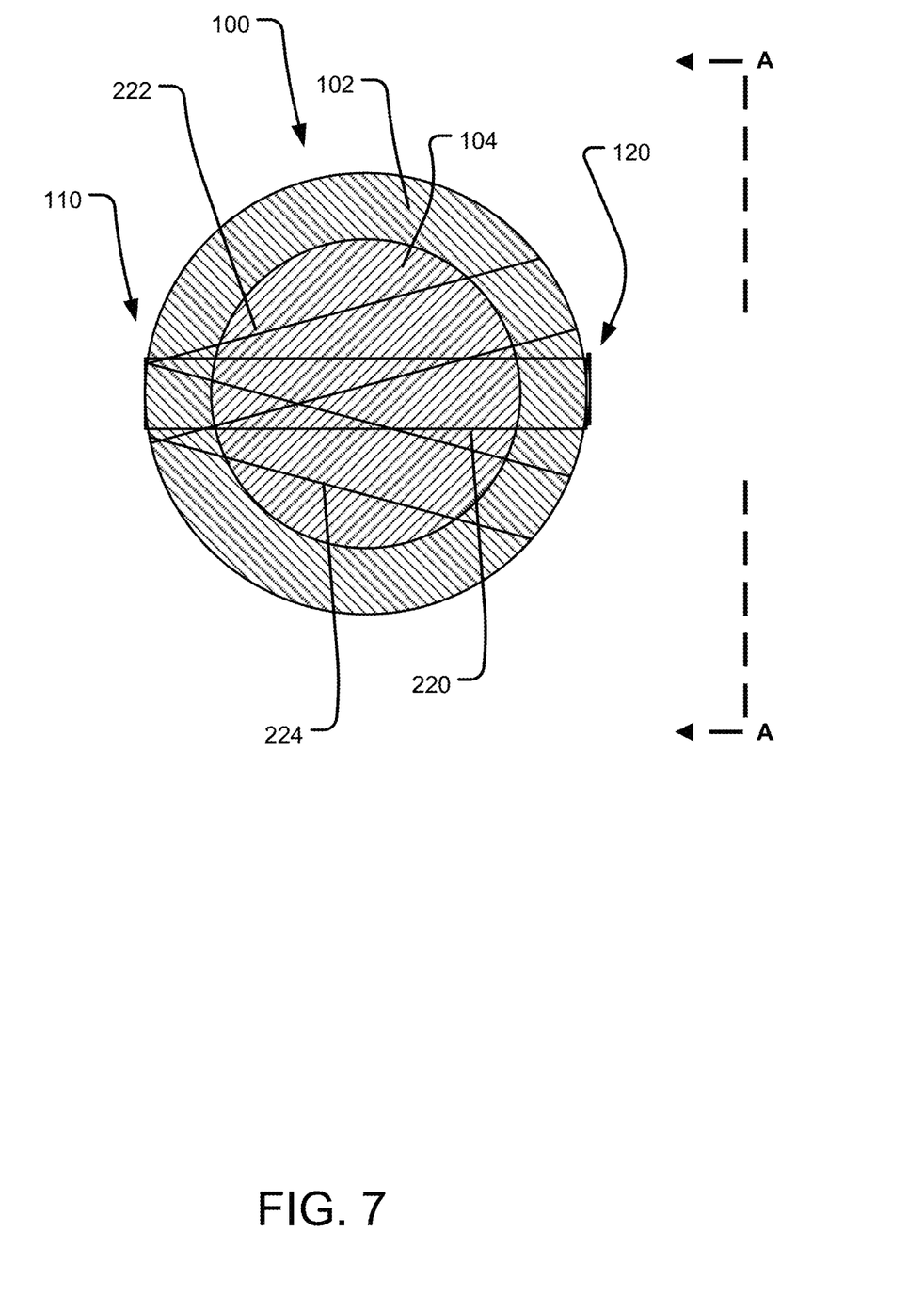
FIG. 7 is a cross sectional view of an example of a bone having a plurality of bores drilled thereto such that a perforated bore structure is created in the bone.
Figure 8:
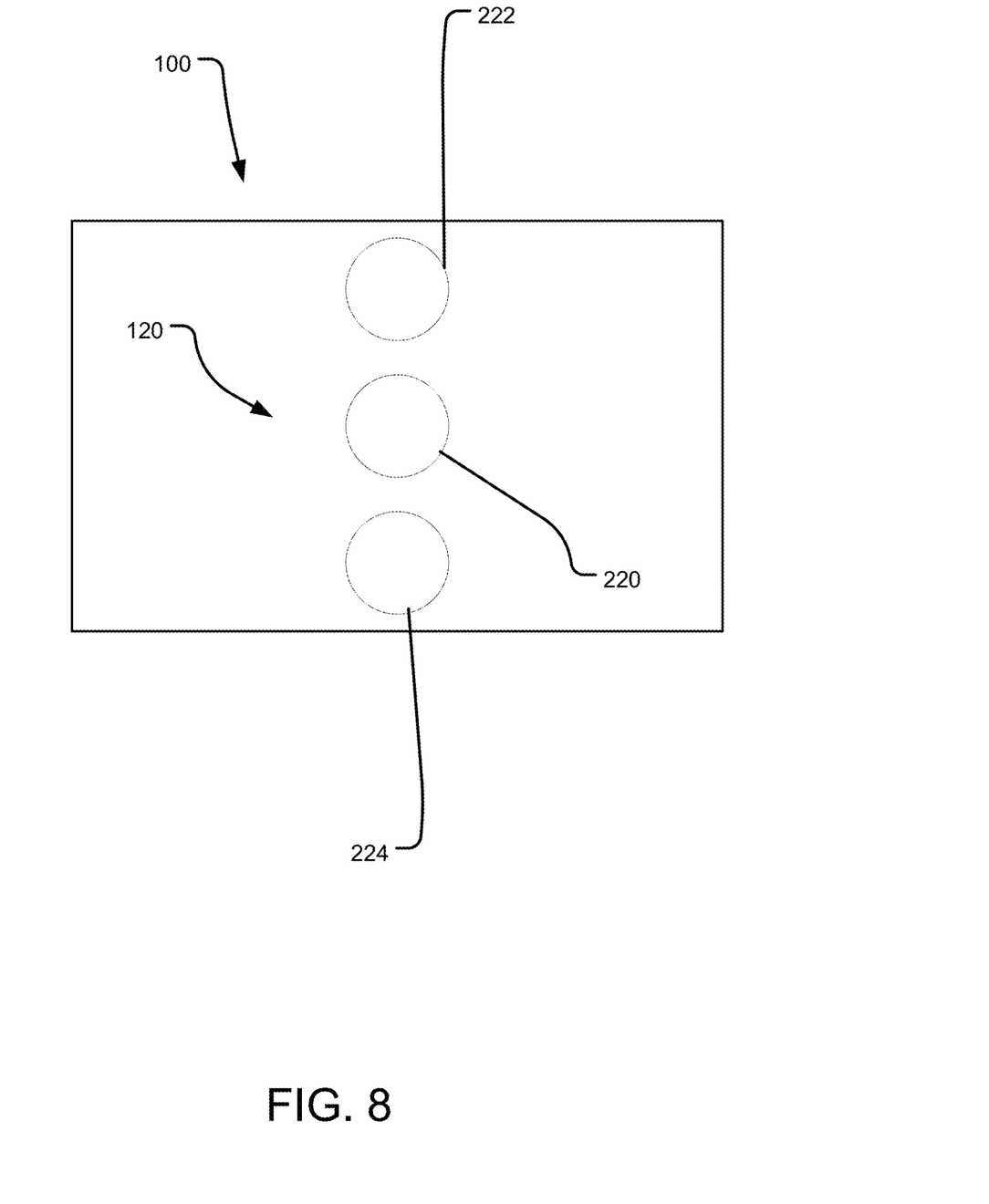
FIG. 8 is a side view taken along section line A-A in FIG. 7 that depicts a distal side of the bone having been drilled.

In any regard, the drill bit 200 may be retraced leaving the first bore 220, the second bore 222, and the third bore 224 as shown in FIG. 7. While three bores are shown, it may be appreciated that additional or fewer bores may be provided without limitation that extend from the proximal side 110 to the distal side 120 of the bone 100. Each bore 220, 222, and 224 may generally pass through the cortex layer 102 at the distal side 120. In turn, with further reference to FIG. 8 taken along section line A-A in FIG. 7, the distal side 120 of the bone 100 may be perforated by the bores 220, 222, and 224. In this regard, the bone 100 may be partially separated. This may allow the cortex layer 102 to more easily be separated or otherwise manipulated (e.g., while allowing portions of the medullary layer 104 between the bores to remain intact). Thus, the multi-directional drilling approach described above to create the perforated distal side 120 of the bone may be used in a corticotomy in a manner that, because the drill bit 200 is prevented from plunging through the distal side 120 of the cortex layer 102, reduced soft tissue damage adjacent to the distal side 120. For example, the perforation of the cortex layer 102 at the distal side 120 of the bone 100 may allow the bone to be fractured in a controlled manner between the bores 220, 222, and 224. The bone 100 may also be fractured between bore 222 and the exterior of the bone 100 and between bore 224 and the exterior of the bone 100. In this regard, the bone 100 may be completely separated to allow for extension or reduction of length. This may be accomplished with minimal trauma to the bone tissue (e.g., with reduced thermal load on the bone tissue) and with minimal exposure of the distal side 120 of the bone 100.

Figure 9:
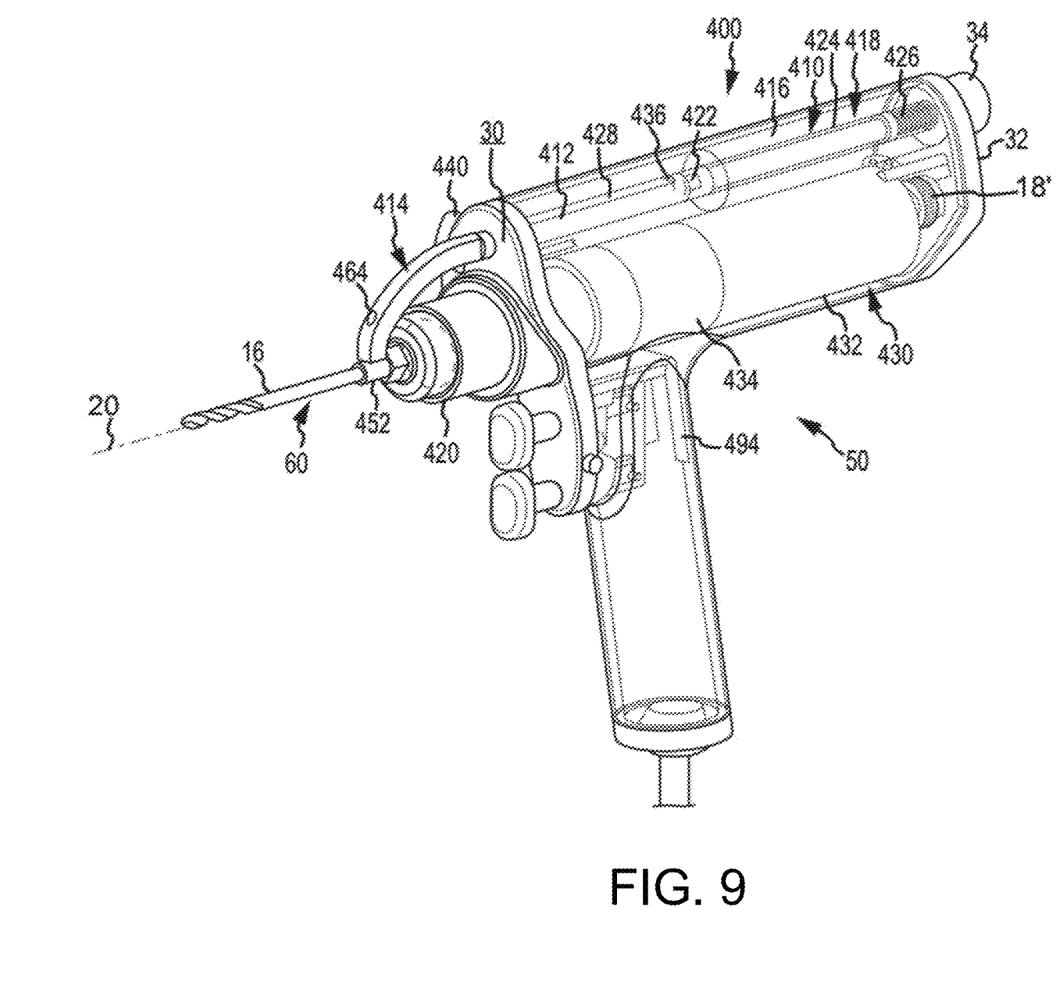
FIG. 9 is a partially cut away view of an example of a drill having a measurement system which may be used in connection with a method for drilling.

FIG. 9 depicts an example of a drill 50 having a measurement system 400 capable of detecting the leading edge 202 of a drill bit 200 passing from the cortex layer 102 to an exterior of the bone 100. Examples of acceptable instruments with such capability are described in detail in U.S. Pat. Nos. 6,665,948, 9,370,372, 9,833,244, U.S. Pat. Pub. No. 2016/0128704, U.S. Pat. Pub. No. 2017/0143440, U.S. Pat. Nos. 10,321,921, and 10,321,920, each of which is incorporated by reference in its entirety herein for all it discloses and teaches.

In any regard, the drill includes an embodiment of a measurement system 400. The drill 50 may be adapted for use with a drill bit assembly 60 that may include a bushing 452. The drill 50 may integrally comprise at least some components of the measurement system 400 to facilitate operation of the measurement system 400 in connection with the drill 50 that may be used to detect an interface between the cortex layer 102 and an exterior of the bone 100. For example, at least a portion of a displacement sensor 410 may be integrated into a housing of the drill 50. In this regard, the displacement sensor 410 may include a displacement sensing arm 412 that is specifically adapted for engagement with a bushing 452 of a drill bit assembly 60 that may be engaged by the chuck 420 of the drill 50.

In this regard, the displacement sensing arm 412 may be used to establish a reference point from which displacement of the drill bit 16 may be measured as described above. In this regard, as follows herein, a general description of the features and operation of the drill 50 used in conjunction with the drill bit assembly 60 is provided.

The displacement sensor 410 may include a displacement sensing arm 412 that may extend from the drill housing. For example, the displacement sensing arm 412 may extend distally (e.g., from a distal face 30 of the drill housing) in a direction corresponding with the direction in which the drill bit 16 extends from a chuck 420 of the drill 50. At least a portion of the displacement sensing arm 412 may extend from the drill housing parallel to an axis of rotation 20 of the drill 50. The displacement sensing arm 412 may also include a distal portion 414 that is adapted to engage a bushing 452 provided with the drill bit assembly 60. As used herein, distal may correspond to a direction from the drill 50 toward the leading edge 16a of the drill bit 16 and proximal may correspond to a direction from the leading edge 16a of the drill bit 16 toward the drill 50. In this regard, at least a portion of the displacement sensing arm 412 (e.g., the distal portion 414) may be adapted to engage the bushing 452 of the drill bit assembly 60 as will be described in more detail below. In any regard, at least a portion of the displacement sensing arm 412 may extend into the housing. The housing may contain a coil 416. As such, a proximal end 418 of the displacement sensing arm 412 may interface with the coil 416 of the displacement sensor 410 that may be disposed within the drill housing.

The displacement sensing arm 412 is shown in a retracted position relative to the drill bit 16. As such, this retracted position shown in FIG. 9 may occur when the drill bit 16 is advanced relative to the bushing 452 during drilling (e.g., such that the portion of the drill bit extending beyond the distal edge of the bushing 452 would be disposed in the medium to be drilled). In this regard, the proximal end 418 of the displacement sensing arm 412 is disposed within the coil 416 of the displacement sensor 410. Accordingly, the displacement sensor 410 may comprise an LVDT sensor as described above that is adapted to sense the position of a core 422 relative to a coil 416. The displacement sensing arm 412 may incorporate a core 422 at the proximal end 418 thereof. Accordingly, as the proximal end 418 of the displacement sensing arm 412 is moved relative to the coil 416, the location of the core 422 may be determined to provide an output corresponding to the position of the core 422, and in turn the displacement sensing arm 412 relative to the drill housing. That is, the displacement sensing arm 412 may be displaceable relative to the coil 416 such that the displacement sensor 410 may be operable to sense a change in position of the displacement sensing arm 412 relative to the drill housing and output a measure of the displacement that may be used as described above in determining a depth of a bore. In an embodiment, the total measurable travel of the core 422 relative to the coil 416 may be at least about 2.5 in (6.4 cm). Furthermore, the resolution of the output of the displacement sensor 410 may be about 0.1% (e.g., about 0.002 inches (0.6 mm) for a sensor having a total measureable travel of 2.5 inches).

While a LVDT displacement sensor is shown and described in relation to the drill 50 shown in the accompanying figures, it may be appreciated that other types of displacement sensors may be provided. For instance, the sensor may provide for the absolute or relative measurement of the position of the distal end of the displacement sensing arm 412 to provide a displacement measure. For instance, in another embodiment, an optical displacement sensor may be provided. Other types of displacement sensors are also contemplated such as, for example, a capacitive displacement sensor, ultrasonic sensors, Hall effect sensors, or any other sensors known in the art capable of outputting an absolute or relative position measure.

In an embodiment, the coil 416 may define a passage 424 extending at least partially through the housing. Specifically, the passage 424 may extend from a proximal face 32 of the housing to the distal face 30 of the housing. That is, the passage 424 may extend entirely though the housing. An end cap 34 may be provided that is operable to close the proximal end of the passage 424 at the proximal face 32 of the drill housing. Furthermore, a biasing member 426 (e.g., a coil spring) may be provided in the passage 424 at a proximal end thereof. The biasing member 426 may be provided between the end cap 34 and the proximal end 418 of the displacement sensing arm 412. In this regard, the biasing member 426 may act on the proximal end 418 of the displacement sensing arm 412 to bias the displacement sensing arm 412 distally relative to the passage 424 and drill housing.

The distal portion 414 of the displacement sensing arm 412 may be adapted to engage a drill bit assembly 60 (e.g., a bushing 452 thereof) that is correspondingly adapted for use with the drill 50. For instance, the displacement sensing arm 412 may generally be linear along the proximal end 418 of the displacement sensing arm 412. In this regard, the proximal end 418 may be adapted to be collinear with the passage 424 and moveable within the passage 424. Furthermore, the distal portion 414 of the displacement sensing arm 412 (e.g., the portion distal to the linear portion of the displacement sensing arm 412) may extend from the linear portion of the displacement sensing arm 412 toward the drill bit assembly 60 that may be engaged by the chuck 420 of the drill 50. In this regard, the linear portion of the displacement sensing arm 412 may be substantially parallel to and offset from the axis of rotation 20. The distal portion 414 may extend from the linear portion in a direction corresponding with the offset such that the distal portion 414 extends toward the drill bit assembly 60. This may facilitate engagement between the displacement sensing arm 412 and the bushing 454 of the drill bit assembly 60. As shown, the distal portion 414 may be an at least partially arcuate member extending along a radius of curvature toward the drill bit assembly 60. However, the distal portion 414 may be shaped differently (e.g., the distal portion 414 may be a linear portion extending at an angle or perpendicularly from the proximal end 418 toward the drill bit assembly 60).

What is claimed is:

1. A method for multi-directional drilling of a bone, comprising:
    drilling a first bore through the bone with a drill bit while monitoring a displacement of the drill bit relative to a reference point and a force acting axially on the drill bit;
    detecting, based on the displacement and the force, a leading edge of the drill bit in the first bore passing through an exterior portion of a cortex of the bone;
    retracting the drill bit at least partially relative to the first bore;
    repositioning the drill bit at a proximal portion of the first bore at an angle with respect to the first bore;
    drilling a second bore through the bone with the drill bit while monitoring the displacement and the force, the second bore extending at an angle relative to the first bore; and
    detecting, based on the displacement and the force, a leading edge of the drill bit in the second bore passing through an exterior portion of a cortex of the bone.

2. The method of claim 1, further comprising:
    drilling a plurality of bores through the bone, each of the plurality of bores offset by a respective angle to others of the plurality of bores; and
    detecting, based on the displacement and the force, the leading edge of the drill bit in each respective one of the plurality of bores passing through an exterior portion of the cortex of the bone.

3. The method of claim 2, further comprising:
    stopping rotation of the drill bit in response to the detecting the leading edge of the drill bit passing through the exterior portion of the cortex of the bone.

4. The method of claim 3, wherein the plurality of bores define a perforated cortex portion at a distal portion of the bone opposite the proximal portion.

5. The method of claim 4, wherein a medullary layer of the bone remains intact in areas extending between the plurality of bores.

6. The method of claim 1, wherein the detecting comprises continuously monitoring a measurement system of a drill having a displacement sensor to measure a displacement of the leading edge of the drill bit relative to the reference point and a force sensor to measure an axial force applied to the leading edge of the drill bit.

* * * * *